United States Patent [19]

Hirasawa et al.

[11] Patent Number: 4,591,649
[45] Date of Patent: May 27, 1986

[54] COMPOUNDS BONDABLE TO TOOTH SUBSTRATES

[75] Inventors: Tadashi Hirasawa, Tokyo; Ikuro Harashima, Yokohama, both of Japan

[73] Assignee: G-C Dental Industrial Corp., Tokyo, Japan

[21] Appl. No.: 712,429

[22] Filed: Mar. 18, 1985

[30] Foreign Application Priority Data

Mar. 27, 1984 [JP] Japan .................. 59-58783

[51] Int. Cl.[4] .................. C07D 307/77; C07D 307/92
[52] U.S. Cl. .................. 549/232; 549/236
[58] Field of Search .................. 549/232, 236

[56] References Cited

FOREIGN PATENT DOCUMENTS

| 149277 | 11/1980 | Japan | 549/236 |
| 362006 | 12/1972 | U.S.S.R. | 549/232 |
| 571485 | 10/1977 | U.S.S.R. | 549/232 |

Primary Examiner—Richard L. Raymond
Attorney, Agent, or Firm—Oblon, Fisher, Spivak, McClelland & Maier

[57] ABSTRACT

A compound which is bondable to tooth substrates, and has the following general formula:

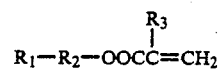

wherein:
$R_1$ is a substituted naphthyl group having a

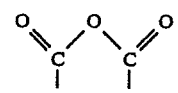

group at any one of the 1,2-, 2,3- and 1,8- positions,
$R_2$ is any of the following groups having any one of carboxylate, carbonyl, and —O— moiety, to be connected to $R_1$:
a group having the formula $-(CH_2)_m-$ in which $m=1-4$,
a group having the formula $-(CH_2)_n-COO-(CH_2)_p-$ in which $n \neq 0$, $p \neq 0$, and $n+p=2-4$, or
a group having the formula $-(CH_2-CH_2O)_q-CH_2-CH_2-$ in which $q=1$ or 2,
wherein when said $R_1$ group is substituted at the 1,2 position, then $R_2$ is bonded to the naphthyl group at any one of the 4, 5, 6 and 7 positions; when said $R_1$ group is substituted at the 2,3 position, then $R_2$ is bonded to the naphthyl group at any one of the 5 and 6 positions; and when said $R_1$ group is substituted at the 1,8 position, then $R_2$ is bonded to the naphthyl group at any one of the 3 and 4 positions, and
$R_3$ is a hydrogen atom or a methyl group.

4 Claims, No Drawings

COMPOUNDS BONDABLE TO TOOTH SUBSTRATES

FIELD OF THE INVENTION

The present invention relates to a compound bondable to tooth substrates which is used alone or in the form of a copolymer with a vinyl compound as a dental bonding agent or dental filling material.

BACKGROUND INFORMATION OF THE PRESENT INVENTION

Heretofore, methyl methacrylate polymers, copolymers of methyl methacrylate with other vinyl compounds, etc. have been used as the dental bonding agents. However, none of these materials have been found to show sufficient adhesion force with respect to dentin. For that reason, procedures such as acid etching of teeth have been relied upon. However, there have arisen the problems of complicating the treatment of teeth, acidifying dentin, etc.

OBJECTS OF THE PRESENT INVENTION

A main object of the present invention is to provide a solution to the aforesaid problems. According to the present invention, that object is for instance achieved by using 6-methacryloxyethyl naphthalene-1,2,6-tricarboxylate anhydride containing hydrophilic and hydrohobic groups:

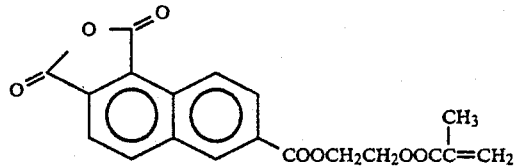

alone or in the form of a resin containing it as a bonding agent or dental filling material, whereby the adhesive force to dentin is improved, and adhesive stability is enhanced.

SUMMARY OF THE INVENTION

According to the present invention, there is provided a compound which is bondable to tooth substrates, and has the following general formula:

$$R_1-R_2-OOCC(R_3)=CH_2$$

wherein:

$R_1$ is a substituted naphthyl group having a

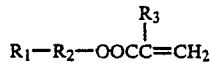

group at any one of the 1,2-, 2,3- and 1,8-positions, $R_2$ is any one of the following groups having any one of carboxylate, carbonyl, and —O— moiety, to be connected to $R_1$:

a group having the formula $-(CH_2)_m-$ in which $m=1-4$, a group having the formula $-(CH_2)_n-COO-(CH_2)_p-$ in which $n \neq 0$, $p \neq 0$, and $n+p=2-4$, or a group having the formula $-(CH_2-CH_2-O)_q-CH_2-CH_2-$ in which $q=1$ or 2, and $R_3$ is a hydrogen atom or a methyl group.

That naphthyl group shows adhesion to tooth substrates, and specifically includes:

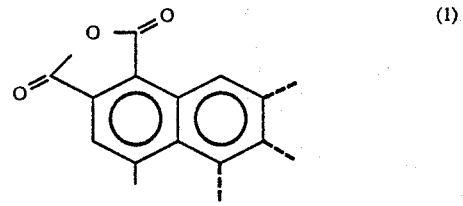

(1)

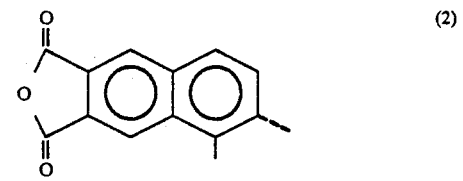

(2)

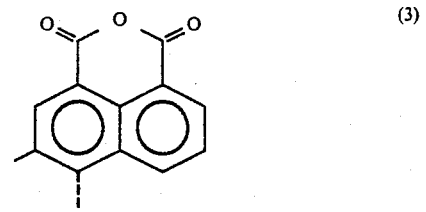

(3)

$R_2$ specifically embraces:

$-COO-(CH_2)_m-$ (m=1-4)

$-CO-(CH_2)_m-$ (m=1-4)

$-O-(CH_2)_m-$ (m=1-4)

$-COO-(CH_2)_n-COO-(CH_2)_p-$ (n≠0, p≠0, n+p=2-4)

$-CO-(CH_2)_n-COO-(CH_2)_p-$ (n≠0, p≠0, n+p=2-4)

$-O-(CH_2)_n-COO-(CH_2)_p-$ (n≠0, p≠0, n+p=2-4)

$-COO-(CH_2CH_2O)_q-CH_2CH_2-$ (q=1 or 2)

$-CO-(CH_2CH_2O)_q-CH_2CH_2-$ (q=1 or 2)

$-O-(CH_2CH_2O)_q-CH_2CH_2-$ (q=1 or 2)

Group $R_2$ is bonded to the naphthyl group by way of any one of the carboxylate, carbonyl and oxy groups it contains. It is noted, however, that when $R_1$ is expressed in terms of formula (1), $R_2$ is bonded to the naphthyl group at any one of the 4, 5, 6 and 7 positions, when $R_1$ is expressed in terms of formula (2), $R_2$ is bonded to the naphthyl group at the 5 or 6 position, and when $R_1$ is expressed in terms of formula (3), $R_2$ is bonded to the naphthyl group at the 3 or 4 position.

DETAILED DESCRIPTION OF THE INVENTION

The preparation of the compounds according to the present invention will now be explained.

PREPARATION EXAMPLE 1

6-methacryloxyethyl naphthalene-1,2,6-tricarboxylate anhydride of Formula (1)

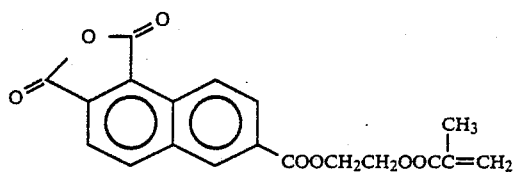

1.50 g (5.76 m mol) of anhydrous naphthalene-1,2,6-tricarboxylic acid chloride and 100 ml of pure benzene are charged into a 300 ml-four-necked flask equipped with a stirrer, a thermometer, a condenser having a calcium chloride tube and 50 ml-branched dropping funnel. Separately, a solution in 50 ml pure benzene of 0.75 g (5.77 m mol) pure 2-hydroxyethyl methacrylate and 0.46 g (5.80 m mol) of pure pyridine is charged into a 50 ml-branched dropping funnel. The flask is cooled therein and maintained at about 5° C. The content of the dropping funnel is added dropwise into the flask. After dropwise addition, stirring is continued overnight at room temperature, and the flask is allowed to stand. The precipitated pyridine hydrochloride is filtered out, and a small amount of hydroquinone monomethyl ether is added to the filtrate-containing benzene solution as the polymerization initiator. The benzene is then distilled off under reduced pressure. The remaining solid is recrystallized twice from carbon tetrachloride for purification, yielding 1.50 g of the refined crystal having a melting point of 118.5° C.-120.0° C.

The infrared spectra of the refined crystal have been found to include absorptions at 3060 cm$^{-1}$ and 1600 cm$^{-1}$, indicative of the presence of a naphthyl group, absorptions at 1840 cm$^{-1}$ and 1775 cm$^{-1}$, indicative of the presence of a 5-member ring acid anhydride, absorptions at 1720 cm$^{-1}$, 1275 cm$^{-1}$ and 1170 cm$^{-1}$, indicative of the presence of esters, and absorption at 1630 cm$^{-1}$, indicative of the presence of a double bond. In the nuclear magnetic resonance spectra, there have been found absorption of δ1.97 at an integrated intensity ratio of 3, indicative of the presence of a methyl group, absorptions of δ4.42-4.68 at an integrated intensity ratio of 4, indicative of the presence of a —CH$_2$—CH$_2$- group, absorptions of δ5.52 and 6.05 at an integrated intensity ratio of 2, indicative of the presence of a H$_2$C=group, and absorptions of δ7.90-8.70 at an integrated intensity ratio of 5, indicative of the presence of an 1,2,6-substituted naphthyl group. The results of further elementary analysis were: carbon:hydrogen=64.14:3.81 (calculated: carbon:hydrogen=64.40:3.95). From these results, the obtained synthetic compound has been determined to be 6-methacryloxyethyl naphthalene-1,2,6-tricarboxylate anhydride of Structural formula (I).

PREPARATION EXAMPLE 2

4-methacryloxyethoxycarbonylpropionoyl-1,8-naphthalic anhydride of the following Structural formula (II)

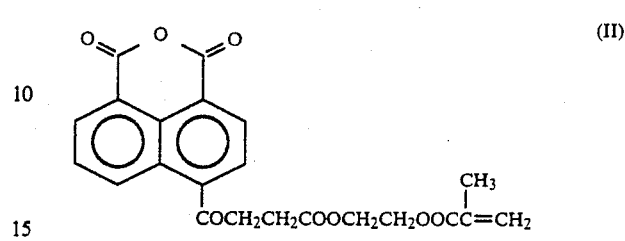

1.27 grams (4 m mol) of a chloride of 3-[(1',8'-anhydrous dicarboxyl)naphthaloyl]propionic acid and 100 ml of pure benzene are charged into a 300 ml-four-necked flask having a stirrer, a thermometer, a condenser equipped with a calcium chloride tube and a 50 ml-branched dropping funnel. Separately, 0.52 grams (4 m mol) of pure of 2-hydroxyethyl methacrylate and 0.32 grams (4 m mol) of pure pyridine are dissolved in 50 ml of pure benzene, and are charged into a 50 ml-branched dropping funnel. Subsequent synthesis of the end product is the same as that of Preparation Example 1. However, the resulting crude crystal is column-chromatographied off, and recrystallized from carbon tetrachloride. The thus refined crytal had a melting point of 108.5° C.-110.0° C., and was obtained in an amount of 0.30 grams.

It has been found that the infrared spectra of the refined crystal includes absorptions at 3070 cm$^{-1}$ and 1595 cm$^{-1}$, indicative of the presence of a naphthyl group, absorptions at 1780 cm$^{-1}$ and 1740 cm$^{-1}$, indicative of the presence of a six-member ring acid anhydride, absorptions at 1725 cm$^{-1}$, 1715 cm$^{-1}$, 1300 cm$^{-1}$ and 1155 cm$^{-1}$, indicative of the presence of esters, and absorption at 1640 cm$^{-1}$, indicative of the presence of a double bond. Nuclear magnetic resonance spectroscopy has also shown that absorption of δ1.98, indicative of the presence of a methyl group, is observed at an integrated intensity ratio of 3, absorptions of δ4.55-4.81, indicative of the presence of two —CH$_2$—CH$_2$-groups, are observed at an integrated intensity ratio of 8, absorptions of δ5.63 and 6.18, indicative of the presence of a H$_2$C=group, are observed at an integrated intensity ratio of 2, and absorptions of δ7.85-9.38, indicative of the presence of an 1,4,8,-substituted naphthyl group, are observed at an integrated intensity ratio of 5. Furthermore, the results of further elementary analysis were carbon:hydrogen=64.29:4.42 (calculated: carbon:hydrogen=64.39:4.42). From the results, the thus obtained synthetic compound has been identified to be 4-methacryloxyethoxycarbonylpropionoyl-1,8-naphthalic anhydride expressed by Formula (II).

According to the present invention, the compound of the general formula:

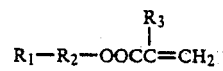

wherein:

R$_1$ is a substituted naphthyl group having a

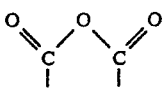

group at 1,2- or 2,3- or 1,8-positions, $R_2$ is any one of the following groups having any one of carboxylate, carbonyl, and —O— moiety, to be connected to $R_1$:

a group having the formula —$(CH_2)_m$— in which $m = 1$–$4$, a group having the formula —$(CH_2)_n$—COO—$(CH_2)_p$— in which $n \neq 0$, $p \neq 0$, and $n + p = 2$–$4$, or a group having the formula —$(CH_2$—$CH_2$—$O)_q$—$CH_2$—$CH_2$— in which $q = 1$ or $2$, and $R_3$ is a hydrogen atom or a methyl group, shows large bonding strength to tooth substrates, and is stable after bonding, since that compound is a hydrophilic/phobic one having in the same molecule hydrophilic group showing a bonding property to tooth substrates and a hydrophobic group rendering a bonding agent, once set, water resistant.

As will be appreciated from the Examples 1 to 7, given later, this compound may be used alone, or in the form of a comonomer with a small amount of a methacrylate monomer or a mixture with two compounds. In either case, high bonding strength is achieved, and it is less likely that a drop of bonding strength may take place even upon immersion in water. This shows that the compound of the present invention has a stable bonding property even in the moistful oral environment.

The present invention will now be explained in detail with reference to the following non-restrictive examples.

The bonding force with respect to tooth substrate was measured with the compounds according to Preparation Examples 1 and 2 as well as 6-methacryloxyethyl naphthalene-2,3,6-tricarboxylate anhydride a melting point of 189°–191° C. of Formula (III).

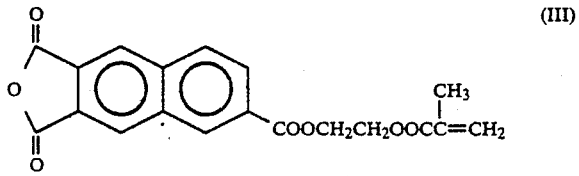

EXAMPLE 1

SAMPLE TO BE BONDED: Bovine Tooth Enamel
BONDING AGENT: 6-methacryloxyethyl naphthalene-1,2,6-tricarboxylate anhydride A bovine foretooth was polished with emery paper No. 1000 to obtain enamel onto which was applied a cellophane tape (about 10×10 mm) having a round hole of 3 mm in diameter. Using a small brush the round hole was coated therein with a 3 wt % chloroform solution of 6-methacryloxyethyl naphthalene-1,2,6-tricarboxylate anhydride. Thereafter, the round hole was therein coated further, by means of another brush, with a methylmethacrylate solution containing as a polymerization initiator an oxidized tri-n-butyl borane, to which a small amount of poly(methyl methacrylate) powder was added. An acryl bar of 4 mm in diameter was then bonded to the enamel. After the lapse of 30 minutes, the cellophane tape was peeled off, and the tooth, to which the acryl bar was still bonded, was immersed in water of 37° C. for 24 hours. After removing the teeth from in the water, the teeth were peeled out of the acryl bar at a tensile rate of 1 mm/minute with the use of Shimazu Autograph IS-500 Model to measure the peeling force. That force was 32 kg/cm². It is to be noted that the same procedures for measuring the peeling force were applied in the following examples.

EXAMPLE 2

SAMPLE TO BE BONDED: Bovine Tooth Enamel
BONDING AGENT: 6-methacryloxyethyl naphthalene-1,2,6-tricarboxylate anhydride + methyl methacrylate + poly(methyl methacrylate)

To make a bonding between a bovine tooth and an acryl bar, the procedures of Example 1 were repeated, provided however that the step of coating a 3 wt % chloroform solution of 6-methacryloxyethyl naphthalene-1,2,6-tricarboxylate anhydride was dispensed with, and use was made of a mixture of 3 wt % of 6-methacryloxyethyl naphthanlene-1,2,6-tricarboxylate anhydride and 97 wt % of methyl methacrylate, said mixture containing as the polymerization initiator an oxidized tri-n-butyl borane and being added with a small amount of poly(methyl methacrylate) powder. The peeling force was 55 kg/cm².

COMPARISON EXAMPLE 1

The procedures of Example 2 were repeated, except that use was made of methyl methacrylate free from 6-methacryloxyethyl naphthalene-1,2,6-tricarboxylate anhydride. The peeling force was 16 kg/cm².

EXAMPLE 3

SAMPLE TO BE BONDED: Bovine Tooth Dentin
BONDING AGENTS:
(a) 6-methacryloxyethyl naphthalene-1,2,6-tricarboxylate anhydride (1) + methyl methacrylate + poly(methyl methacrylate)
(b) 6-methacryloxyethyl naphthalene-2,3,6-tricarboxylate anhydride (2) + methyl methacrylate + poly(methyl methacrylate)
(c) 4-methacryloxyethoxycarbonylpropionoyl-1,8-naphthalic anhydride (3) + methyl methacrylate + poly(methyl methacrylate)

While tapping water, the enamel of a bovine foretooth surface was carefully polished off to expose the dentin to view, which was in turn polished smoothly with emery paper No. 1000. Thereafter, a cellophane tape (about 10 mm×10 mm) having a round hole of 3 mm in diameter was applied to the dentin surface. Using an oxidized tri-n-butyl borane as the polymerization initiator, a bonding agent composition was prepared, which comprised a mixture of 3% by weight of the aforesaid compound (1) and 97% by weight of methyl methacrylate, said mixture containing a small amount of poly(methyl methacrylate) powder. That composition was coated into the aforesaid round hole with a small brush to bond an acryl bar to the dentin of the bovine tooth. In a similar manner, an acryl bar was bonded to the dentin of a bovine tooth with a bonding agent composition using the compound (2) or (3) for the compound (1). The resulting peeling forces were measured.

COMPARISON EXAMPLE 2

The same procedures as in Example 3 were applied using as the monomer methyl methacrylate alone in the absence of the compounds (1), (2) and (3). The resulting peeling forces were measured.

The results of Example 3 and Comparison Example 2 are set forth in Table 1.

TABLE 1

| | Bonding Agent Composition (Wt. %) | | Peeling Force (kg/cm$^2$) |
|---|---|---|---|
| Example 3 | 6-methacryloxyethyl naphthalene-1,2,6-tricarboxylate anhydride | 3 | 48 |
| | Methyl methacrylate | 97 | |
| | 6-methacryloxyethyl naphthalene-2,3,6-tricarboxylate anhydride | 3 | 51 |
| | Methyl methacrylate | 97 | |
| | 4-methacryloxyethoxycarbonyl-propionoyl-1,8-naphthalic anhydride | 3 | 44 |
| | Methyl methacrylate | 97 | |
| Comparison Example 2 | Methyl methacrylate | 100 | 25 |

EXAMPLE 4

SAMPLE TO BE BONDED: ENAMEL AND DENTIN OF BOVINE TOOTH treated with a citric acid and ferric chloride-containing aqueous solutions
BONDING AGENTS: the same as used in Ex. 3

The enamel of a bovine tooth as described in Ex. 1 and the dentin of a bovine tooth as described in Ex. 3 were treated for 30 seconds with an aqueous solution containing 10% by weight of citric acid and 3% by weight of ferric chloride, respectively. Acryl bars were then bonded to the bovine teeth according to the procedures of Ex. 3. The teeth to which the acryl bar was bonded were immersed in water of 37° C. for 24 hours, after which the peeling force was measured. Another teeth to which the acryl bar was bonded were immersed in waters of 4° C. and 60° C. 60 times for a total of 2 hours, alternately every 1 minute, after which the peeling force was measured.

COMPARISON EXAMPLE 3

To measure peeling forces, similar experiments were carried out using as the monomer methyl methacrylate alone in the absence of the compounds corresponding to (1), (2) and (3) in Ex. 4.

The results of Example 4 and comparison Example 3 are set forth in Table 2.

EXAMPLE 5

SAMPLE TO BE BONDED: the same as used in Ex. 4
BONDING AGENT: 6-methacryloxyethyl naphthalene-1,2,6-tricarboxylate anhydride+methyl methacrylate+poly(methyl methacrylate)

Example 4 was repeated, except that a compostion of 3% by weight of 6-methacryloxyethyl naphthalene-1,2,6-tricarboxylate anhydride, 97% by weight of methyl methacrylate and a small amount of poly(methyl methacrylate) powder was used as the bonding agent, and the test pieces were immersed in waters of 4° C. and 60° C. 120 times for a total of 4 hours, alternately every 1 minute. The peeling forces were 128 kg/cm$^2$ with respect to enamel, and 127 kg/cm$^2$ with respect to dentin.

COMPARISON EXAMPLE 4

Example 5 was repeated, except that only methyl methacrylate was used in the absence of 6-methacryloxyethyl naphthalene-1,2,6-tricarboxylate anhydride. The peeling forces were 85 kg/cm$^2$ with respect to enamel, and 53 kg/cm$^2$ with respect to dentin.

COMPARISON EXAMPLE 5

Example 5 was repeated, except that a bonding agent was used to the dentin of a bovine tooth as used in Ex. 4, said bonding agent being obtained by adding a small amount of poly(methyl methacrylate) powder to a mixture of 5% by weight of 4-methacryloxyethyl trimellitate anhydride and 95% by weight of methyl methacrylate, and designed to be set by polymerization initiator of an oxidized tri-n-butyl borane. The peeling force was 97 kg/cm$^2$.

EXAMPLE 6

SAMPLE TO BE BONDED: the same as used in Ex. 4
BONDING AGENT: 6-methacryloxyethyl naphthalene-1,2,6-tricarboxylate anhydride+6-methacryloxyethyl naphthalene-2,3,6-tricarboxylate anhydride+methyl methacrylate+poly(methyl methacrylate)

Examples 4 and 5 were repeated, except that acryl bars were bonded to bovine teeth with a bonding agent obtained by adding a small amount of poly(methyl methacrylate) powder to a mixture of 2.5% by weight of 6-methacryloxyethyl naphthalene-1,2,6-tricarboxylate anhydride, 2.5% by weight of 6-methacryloxyethyl naphthalene-2,3,6-tricarboxylate anhydride and 95% by weight of methyl methacrylate, wherein an oxidized tri-n-butyl borane was used as the polymerization initia-

TABLE 2

| | Bonding Agent Composition (% by weight) | | 24 hrs after immersion in water | | After 60 times of alternate immersion | |
|---|---|---|---|---|---|---|
| | | | Enamel | Dentin | Enamel | Dentin |
| Example 4 | 6-methacryloxyethyl naphthalene-1,2,6-tricarboxylate anhydride | 3 | 158 | 130 | 142 | 149 |
| | Methyl methacrylate | 97 | | | | |
| | 6-methacryloxyethyl naphthalene-2,3,6-tricarboxylate anhydride | 3 | 152 | 140 | 147 | 138 |
| | Methyl methacrylate | 97 | | | | |
| | 4-methacryloxyethoxycarbonylpropionoyl-1,8-naphthalic anhydride | 3 | 137 | 130 | 116 | 113 |
| | Methyl methacrylate | 97 | | | | |
| Comparison Example 3 | Methyl methacrylate | 100 | 121 | 103 | 104 | 63 | tor. The peeling force measurements are shown in Table 3.

TABLE 3

| Immersion Method | | Peeling Force (kg/cm$^2$) | |
|---|---|---|---|
| | | Enamel | Dentin |
| Continued Immersion | After 24 hrs. | 142 | 136 |
| Alternate Immersion | After 60 times | 137 | 144 |
| Alternate Immersion | After 120 times | 124 | 133 |

EXAMPLE 7

SAMPLE TO BE BONDED: ENAMEL AND DENTIN OF HUMAN TEETH treated with aqueous solutions containing citric acid and ferric chloride
BONDING AGENTS: the same as used in Ex. 3

In place of the bovine teeth used in Ex. 3, extracted sound teeth of individuals were employed. The labial sides of such teeth were smoothly polished with emery paper No. 1000 to obtain enamel. On the other hand, a part of the crown portion of extracted sound teeth of individuals was cut vertically along the tooth axis, and smoothly polished with emery paper No. 1000 to obtain dentin. The enamel and dentin were treated with aqueous solutions containing 10% by weight of citric acid and 3% by weight of ferric chloride used in Ex. 4. Other procedures were identical with those of Ex. 3 to measure the peeling forces.

COMPARISON EXAMPLE 6

Example 7 was repeated, except that only methyl methacrylate was used as the monomer in the absence of the compounds corresponding to (1), (2) and (3) in the bonding agent of Ex. 3.

The results of Example 7 and Comparison Example 6 are set forth in Table 4.

TABLE 4

| | Bonding Agent Composition (Wt. %) | | Peeling Force (kg/cm$^2$) | |
|---|---|---|---|---|
| | | | Human Enamel | Human Dentin |
| Example 7 | 6-methacryloxyethyl naphthalene-1,2,6-tricarboxylate anhydride | 3 | 129 | 110 |
| | Methyl methacrylate | 97 | | |
| | 6-methacryloxyethyl naphthalene-1,2,6-tricarboxylate anhydride | 3 | 115 | 117 |
| | Methyl methacrylate | 97 | | |
| | 4-methacryloxyethoxy-carbonylpropionoyl-1,8-naphthalic anhydride | 3 | 72 | 83 |
| | Methyl methacrylate | 97 | | |
| Comparison Example 6 | Methyl methacrylate | 100 | 32 | 32 |

EXAMPLE 8

SAMPLE TO BE BONDED: Bovine Tooth Enamel treated with an aqueous solution containing citric acid and ferric chloride
BONDING AGENT: 6-methacryloxyethyl naphthalene-2,3,6-tricarboxylate anhydride + methyl methacrylate + poly(methyl methacrylate)

The procedures of Example 4 were repeated, except that the bovine tooth enamels as mentioned in Example 4 were used as the sample to be bonded, and a composition containing 1% by weight of 6-methacryloxyethyl naphthalene-2,3,6-tricarboxylate anhydride was used as the bonding agent. After 24 hour-immersion in water of 37° C., the peeling force was 163 kg/cm$^2$, while the peeling force after 60 time-alternate immersion was 148 kg/cm$^2$.

EXAMPLE 9

SAMPLE TO BE BONDED: Bovine Tooth Dentin treated with an aqueous solution containing citric acid and ferric chloride
BONDING AGENT: The same as in Example 8

The procedures of Example 8 were repeated, provided that the bovine dentins as mentioned in Example 4 were employed. After 24 hour-immersion in water of 37° C., the peeling force was 177 kg/cm$^2$, while the peeling force after 60 time-alternate immersion was 135 kg/cm$^2$.

What is claimed is:

1. A compound which is bondable to tooth substrates, having the formula

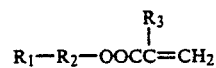

wherein
R$_1$ is a naphthyl group substituted with a

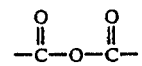

group at any one of the 1,2-; 2,3-; and 1,8 positions, and
R$_2$ is any one of the following groups having any one of carboxylate, carbonyl, and —O— moiety, to be connected to R$_1$:
a group having the formula —(CH$_2$)$_m$— in which m=1–4,
a group having the formula —(CH$_2$)$_n$—COO—(CH$_2$)$_p$— in which n≠0, p≠0, and n+p=2–4, or
a group having the formula —(CH$_2$—CH$_2$—O)$_q$—CH$_2$—CH$_2$— in which q=1 or 2,
wherein when said R$_1$ group is substituted at the 1,2 position, then R$_2$ is bonded to the naphthyl group at any one of the 4, 5, 6 and 7 positions; when said R$_1$ group is substituted at the 2,3 position, then R$_2$ is bonded to the naphthyl group at any one of the 5 and 6 positions; and when said R$_1$ group is substituted at the 1,8 position, then R$_2$ is bonded to the naphthyl group at any one of the 3 and 4 positions, and
R$_3$ is a hydrogen atom or a methyl group.

2. The compound of claim 1 which is 6-methacryloxyethyl naphthalene-1,2,6-tricarboxylate anhydride.

3. The compound of claim 1 which is 4-methacryloxyethoxycarbonylpropionoyl-1,8-naphthalic anhydride.

4. The compound of claim 1 which is 6-methacryloxyethyl naphthalene-2,3,6-tricarboxylate anhydride.